United States Patent [19]
Ramsey et al.

[11] Patent Number: 5,584,840
[45] Date of Patent: Dec. 17, 1996

[54] UMBILICAL CORD CUTTING AND CLAMPING DEVICE

[76] Inventors: James E. Ramsey, 23111 Marvilla La., Coto de Caza, Calif. 92679; Gregg E. Plambeck, 2868 Via Bellota, San Clemente, Calif. 92673

[21] Appl. No.: 523,416

[22] Filed: Sep. 5, 1995

[51] Int. Cl.$^6$ .......................... A61B 17/00; A61B 17/12
[52] U.S. Cl. .......................... 606/120; 606/151
[58] Field of Search .................. 606/120, 151, 606/157, 158, 167

[56] References Cited

U.S. PATENT DOCUMENTS

| | | | |
|---|---|---|---|
| 3,106,919 | 10/1963 | Churchville | 606/120 |
| 3,323,208 | 6/1967 | Hurley, Jr. | 30/124 |
| 3,631,858 | 1/1972 | Ersek | 128/318 |
| 4,026,294 | 5/1977 | Mattler | 128/305 |
| 4,716,886 | 1/1988 | Schulman et al. | 128/305 |
| 4,781,188 | 11/1988 | Collins | 128/305 |
| 4,856,517 | 8/1989 | Collins et al. | 128/346 |
| 4,938,215 | 7/1990 | Schulman et al. | 606/120 |
| 5,009,657 | 4/1991 | Cotey et al. | 606/120 |
| 5,190,556 | 3/1993 | Hessel | 606/120 |
| 5,415,665 | 5/1995 | Hessel et A. | 606/120 |
| 5,462,555 | 10/1995 | Bolanos et al. | 606/120 |

FOREIGN PATENT DOCUMENTS 8504091  9/1985  WIPO .................. 606/120

OTHER PUBLICATIONS

Faxed copy of "Cordguard" brochure from Utah Medical. Brochure is date Jun. 3, 1994. (This is the only copy available).

Primary Examiner—Sam Rimell
Assistant Examiner—Benjamin K. Koo
Attorney, Agent, or Firm—Jack Lo

[57] ABSTRACT

An umbilical cord cutting and clamping device includes first and second clamps held in a side-by-side abutting relation. Each clamp includes first and second arms hingeably connected at a first end, and gripping surfaces arranged on the interior of the arms. A blade is attached to the first arm of the first clamp and project into a space between the arms thereof. A pair of side splash guards are attached to abutting first arms on either side of the blade. A pair of front splash guards are attached to the second ends of the second arms and extend toward the first arms. When the clamps are closed around an umbilical cord, the cord is simultaneously clamped by the gripping surfaces and severed by the blade. The splash guards prevent blood from splashing onto surrounding persons when the umbilical cord is severed. The clamps are separable after clamping onto and severing the umbilical cord, so that the baby and the placenta can be separated.

14 Claims, 5 Drawing Sheets

5,584,840

UMBILICAL CORD CUTTING AND CLAMPING DEVICE

BACKGROUND OF THE INVENTION

1. Field Of The Invention

This invention relates generally to umbilical cord clamps, specifically to a device that simultaneously severs and clamps an umbilical cord of a newborn infant.

2. Prior Art

A fetus receives its blood supply and nutrients from its mother through an umbilical cord connected between the baby's abdomen and the mother's placenta. Immediately after the birth of the baby, the umbilical cord is severed to separate the baby from its mother. Blood loss from the mother and baby is typically minimized by clamping the umbilical cord with two slightly spaced clamps before the cord is cut between the clamps. This procedure requires three separate devices—two clamps and a scalpel—and is somewhat time consuming.

Many umbilical cord clamping devices with built-in cutting blades for both cutting and clamping umbilical cords have been proposed. U.S. Pat. No. 4,938,215 to Schulman et al. (1990) shows an umbilical cord clamping device that includes two clamps held together side-by-side by a single shear pin. A lever with a cutting blade is positioned between abutting arms of the clamps and pivotally attached to the hinge of the clamps. The movement of the lever between the arms is impeded by the shear pin. The clamps are closed upon an umbilical cord by pressing the lever downwardly. After the clamps are fully closed, the shear pin is broken by further pressure upon the lever, so that the blade is brought down upon the umbilical cord to sever it. However, breaking the shear pin requires a moderate amount of force, so that the device is somewhat difficult to operate. Furthermore, some blood is splashed outwardly from the device during the instant when the umbilical cord is cut, so that surrounding persons are exposed to the danger of contacting potentially infectious blood.

U.S. Pat. No. 4,856,517 to Collins et al. (1989) shows an umbilical cord clamping device that includes two spaced apart small clamps fitted within a larger clamp for simultaneous closing. After the clamps are closed around an umbilical cord, they are locked in a closed position by a latch. A knob with a blade attached thereto is fitted within a slot in the large clamp between the smaller clamps. The knob is manually moved forwardly to sever the cord with the blade. When the knob has reached the end of the slot, the latch is engaged and released by the knob to allow the opening and removal of the larger clamp, but the small clamps remain clamped around the umbilical cord. This device requires two separate steps to operate, i.e., clamping the cord, and then moving the blade. Furthermore, blood is splashed outwardly from the slot during the cutting operation. This device includes five pans—one large clamp, two small clamps, a knob, and a blade—so that manufacturing cost is relatively high.

U.S. Pat. No. 4,781,188 to Collins (1988) shows an umbilical cord clamping device that includes two spaced apart small clamps fitted within a larger clamp for simultaneous closing. A fixed blade attached to one arm of the larger clamp automatically cuts an umbilical cord when the device is clamped thereon. When the device is released, the larger clamp is opened automatically and separated from the smaller clamps, which are latched closed on the severed ends of the umbilical cord. However, blood will splash outwardly through the front of the larger clamp when the umbilical cord is severed.

U.S. Pat. No. 4,716,886 to Schulman et al. (1988) shows an umbilical cord clamping device that includes two clamps held together side-by-side by a single shear pin. A blade is slidably positioned between abutting arms of the clamps. The movement of the blade between the arm is impeded by the shear pin. The clamps are closed upon an umbilical cord by pressing the blade downwardly. After the clamps are fully closed, the shear pin is broken by further pressure upon the blade, so that the blade is moved inwardly to sever the umbilical cord. However, this device is somewhat difficult to operate, due to the need to break the shear pin. Furthermore, it cannot prevent blood from splashing onto surrounding persons.

U.S. Pat. No. 4,026,294 to Mattler (1977) shows an umbilical cord clamping device that includes two clamps attached to the cutting blades of a scissors-like installation device by breakable bridges. Squeezing the handles of the installation device closes the clamps around the umbilical cord. Squeezing the handles further breaks the bridges to separate the cutting blades from the clamps, and close the blades to sever the umbilical cord. However, this device is relatively complicated to setup and use, and requires many parts, including the relatively expensive installation device.

U.S. Pat. No. 3,631,858 to Ersek (1972) shows an umbilical cord clamping device that includes two clamps held together side-by-side by a long breakable bridge. A cutting blade is fixedly attached to one of the arms. When the clamps are closed upon an umbilical cord, the blade first severs the cord, then breaks the bridge to separate the clamps. However, the device is somewhat difficult to operate, due to the high force necessary to cut the long bridge. It also cannot prevent blood from splashing onto surrounding persons.

U.S. Pat. No. 3,323,208 to Hurley, Jr. (1967) shows an umbilical cord clamping device that includes two clamps held together side-by-side by pins on one clamp frictionally fitted into sockets on an abutting edge of the other clamp. A blade positioned between the clamps cuts the cord when the clamps are closed. However, the short pins cannot reliably hold the clamps together, so that accidental separation can occur. It also cannot prevent blood from splashing onto surrounding persons.

An umbilical cord clamp sold under the trademark "Cordguard" by Utah Medical includes a sliding blade arranged on one of two hingeably connected, lockable arms. After the arms are locked closed around an umbilical cord, the blade is pressed inwardly to sever it. This device is somewhat inconvenient to use, because it requires separate clamping and cutting steps.

OBJECTS OF THE INVENTION

Accordingly the primary object of the present invention is to provide an umbilical cord cutting and clamping device that prevents blood from splashing onto surrounding persons during the cutting process.

Another object of the present invention is to provide an umbilical cord cutting and clamping device that severs and clamps an umbilical cord in a single stroke.

Another object of the present invention is to provide an umbilical cord cutting and clamping device that prevents blood loss from a baby and its mother after it severs the umbilical cord.

Another object of the present invention is to provide an umbilical cord cutting and clamping device that is very easy to install.

Another object of the present invention is to provide an umbilical cord cutting and clamping device that is easily separable into two clamps after clamping.

Yet another object of the present invention is to provide an umbilical cord cutting and clamping device with separable clamps that resist accidental separation or unlocking.

Still another object of the present invention is to provide an umbilical cord cutting and clamping device that is economical to manufacture.

Other objects of the present invention will become apparent from a study of the following description and the accompanying drawings.

SUMMARY OF THE INVENTION

An umbilical cord cutting and clamping device includes first and second clamps positioned side- by-side in abutting relation. Each clamp includes hingeably connected first and second arms that form a "U" shape. The second clamp includes members extending partially into the interior of the first clamp. Shallow ribs on the members engage grooves arranged on the interior of the first clamp, so that the clamps are securely held together, but are easily separable when desired. A cutting blade is arranged inside the first clamp. Closing the clamps around an umbilical cord of a newborn baby clamps and severs it simultaneously. A pair of splash guards arranged on either side of the blade prevents blood from splashing onto surrounding persons. After the clamps are latched closed, they are easily pulled apart to separate the baby from the placenta. The separated clamps remain on the severed ends of the umbilical cord to prevent blood loss.

Figure 1:
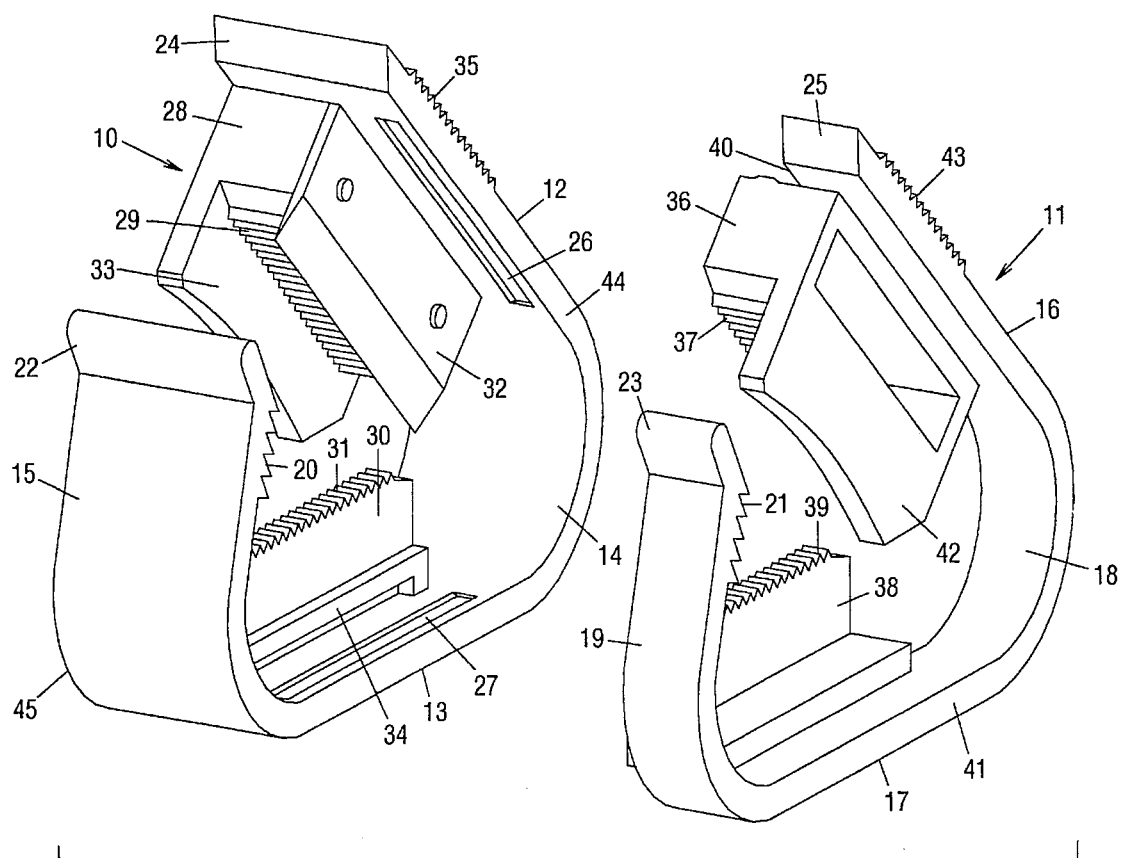
FIG. 1 is a front perspective exploded view of an umbilical cord cutting and clamping device in accordance with a preferred embodiment of the invention.

| Drawing Reference Numerals | |
| --- | --- |
| 10. First Clamp | 11. Second Clamp |
| 12. First Arm | 13. Second Arm |
| 14. Hinge | 15. Front Splash Guard |
| 16. First Arm | 17. Second Arm |
| 18. Hinge | 19. Front Splash Guard |
| 20. Locking Teeth | 21. Locking Teeth |
| 22. Grip Portion | 23. Grip Portion |
| 24. Tapered End | 25. Tapered End |
| 26. Retaining Groove | 27. Retaining Groove |
| 28. Gripping Member | 29. Gripping Surface |
| 30. Gripping Member | 31. Gripping Surface |
| 32. Blade | 33. Side Splash Guard |
| 34. Spacer | 35. Knurls |

| -continued | |
| --- | --- |
| Drawing Reference Numerals | |
| 36. Gripping Member | 37. Gripping Surface |
| 38. Gripping Member | 39. Gripping Surface |
| 40. Abutting Edge | 41. Outer Edge |
| 42. Side Splash Guard | 43. Knurls |
| 44. Abutting Edge | 45. Outer Edge |
| 46. Retaining Rib | 47. Retaining Rib |
| 48. Gap | 49. Umbilical Cord |
| 50. U-Shaped Channel | 51. Combined Clamp |

DESCRIPTION FIG. 1

In accordance with a preferred embodiment of the invention shown in the front perspective view in FIG. 1, an umbilical cord cutting and clamping device includes a first clamp 10 and a second clamp 11. First clamp 10 includes first and second arms 12 and 13, respectively, connected at a first end in an open position by a resilient loop hinge 14 in a "U" shape. A front splash guard 15 is connected to a second end of second arm 13 and extend toward a second end of first arm 12. Second clamp 11 includes first and second arms 16 and 17, respectively, connected at a first end by a loop hinge 18 in an open position in a matching "U" shape. A front splash guard 19 is connected to a second end of second arm 17 and extend toward a second end of first arm 16.

Locking teeth 20 and 21 are arranged on the interior of front splash guards 15 and 19, respectively, and grip portions 22 and 23 are arranged at the distal ends thereof. First arms 12 and 16 include tapered second ends 24 and 25, respectively. A pair of retaining grooves 26 and 27 are positioned longitudinally on the interior surfaces of arms 12 and 13, respectively, adjacent an abutting edge 44. Clamp 10 also includes an outside edge 45.

An elongated gripping member 28 with a serrated gripping surface 29 on its inner side is attached longitudinally to the inside of arm 12, opposite an elongated gripping member 30 with a serrated gripping surface 31 attached longitudinally to the inside of arm 13. A cutting blade 32 is attached to gripping member 28 on the side adjacent abutting edge 44, and a side splash guard 33 is attached to gripping member 28 adjacent outside edge 45. Both blade 32 and splash guard 33 extend substantially ahead of gripping surface 29. A spacer 34 is attached to gripping member 30 on the side adjacent abutting edge 44. Knurls 35 are arranged on the outside of arm 12 for providing a non-slip gripping surface.

An elongated gripping member 36 with a serrated gripping surface 37 is attached longitudinally to the inside of arm 16, opposite a L-beam-shaped gripping member 38 with a serrated gripping surface 39 attached longitudinally to the inside of arm 17. Gripping members 36 and 38 extend laterally beyond an abutting edge 40 of clamp 11. A side splash guard 42 is attached to gripping member 36 on the side adjacent an outside edge 41 of clamp 11. Splash guard 42 extends substantially ahead of gripping surface 37. Knurls 43 are arranged on the outside of arm 16 for providing a non-slip gripping surface.

In this embodiment, clamps 10 and 11 are each molded as integral units from a resilient material, such as nylon or high density polyethylene, with a relatively inexpensive "straight pull" mold, and without the use of slides in the mold. Unlike some prior art devices that include as many as five separate pans, the present umbilical cord cutting and clamping device includes only three parts—two clamps and a blade—so that it is very economical to manufacture.

DESCRIPTION FIG. 2

Figure 2:
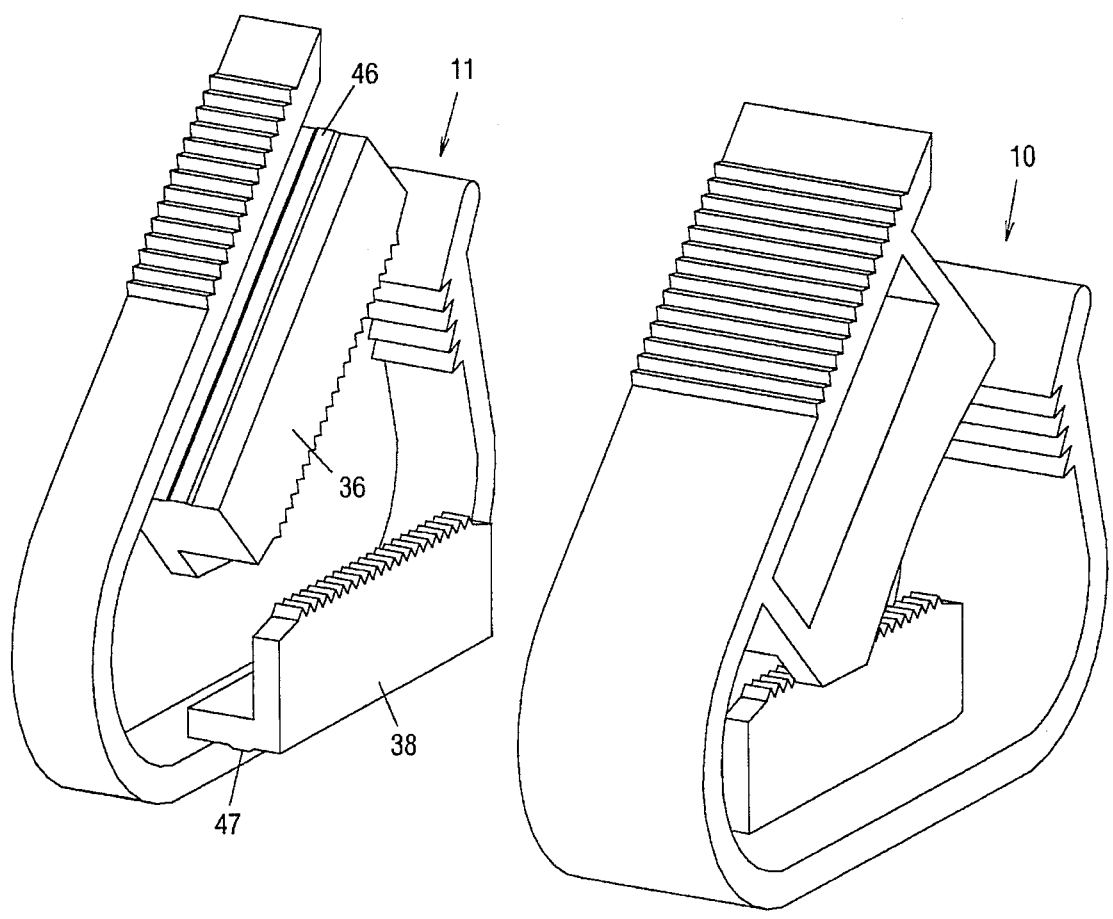
FIG. 2 is a rear perspective exploded view of the umbilical cord cutting and clamping device.

As shown in the rear perspective view in FIG. 2, a pair of retaining ribs 46 and 47 are arranged longitudinally on the outside surfaces of gripping members 36 and 38, respectively.

DESCRIPTION FIG. 3

Figure 3:
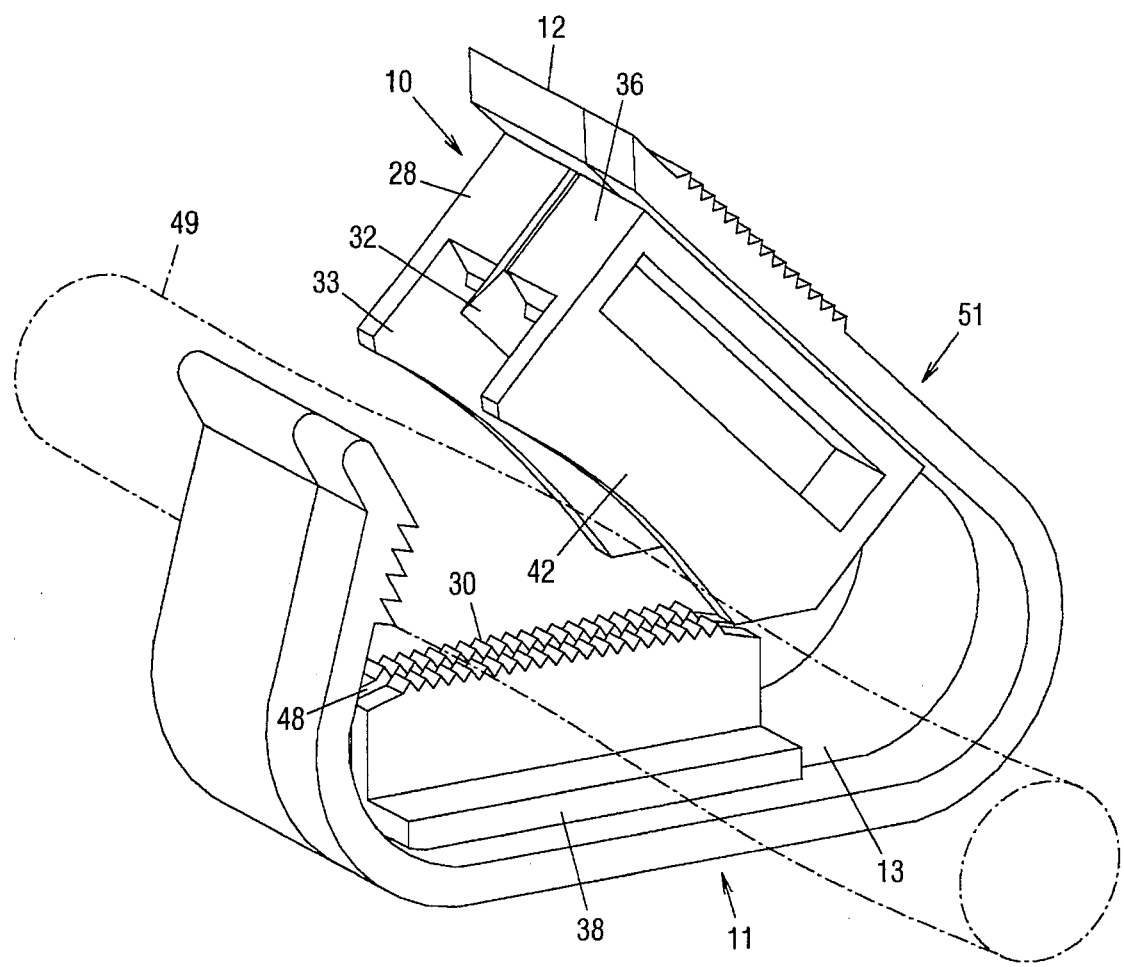
FIG. 3 is a side perspective view of the umbilical cord cutting and clamping device in an assembled and open condition.

Clamps 10 and 11 are shown assembled together to form a single clamp 51 in the side perspective view in FIG. 3. Gripping members 36 and 38 are in engagement with the interior surfaces of arms 12 and 13, respectively. Blade 32 is positioned between gripping members 28 and 36. Side splash guards 33 and 42 are positioned on either side of blade 32, and extend substantially ahead of the cutting edge thereof. A gap 48 is formed between gripping members 30 and 38.

To use, the umbilical cord cutting and clamping device is positioned around an umbilical cord 49, with clamp 10 positioned on the side of the placenta (not shown), and clamp 11 positioned on the side of the newborn baby (not shown). The concave forward edges of splash guards 33 and 42 serve to position umbilical cord 49 under blade 32.

DESCRIPTION FIG. 4

Figure 4:
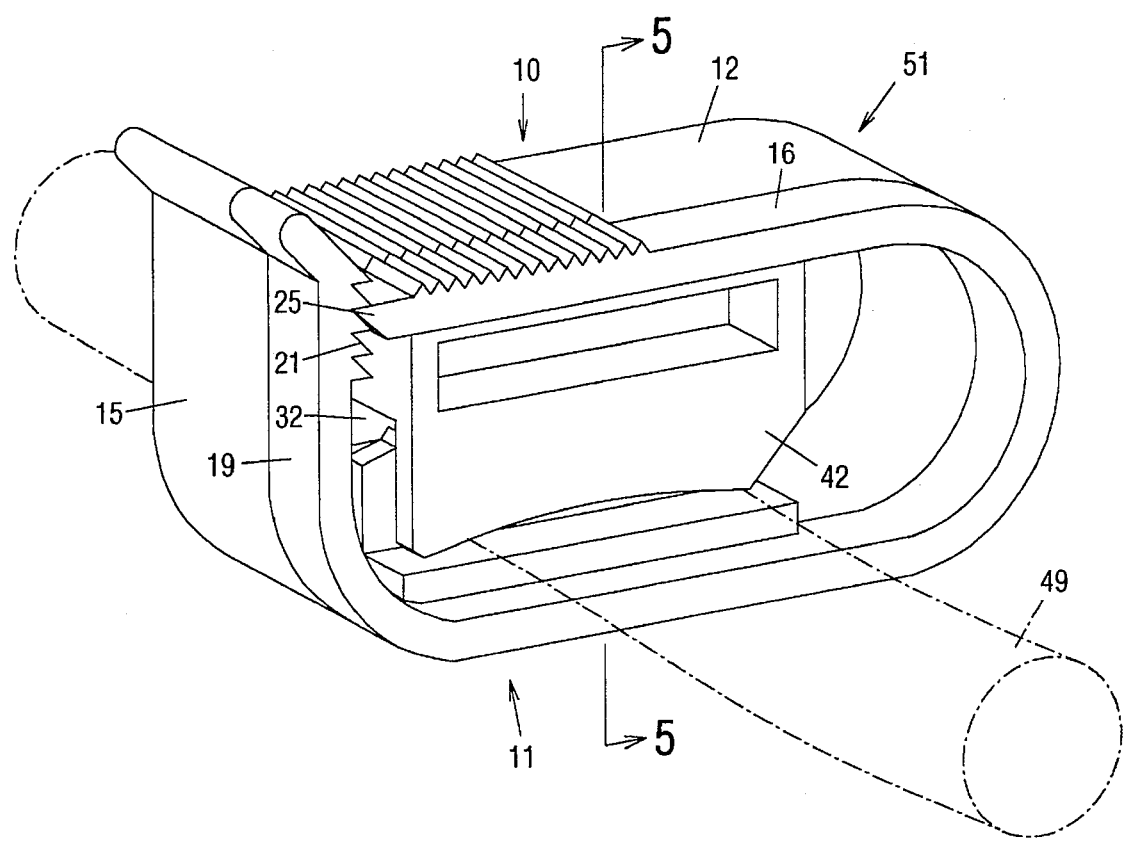
FIG. 4 is a side perspective view of the umbilical cord cutting and clamping device in a closed condition.

As shown in the side perspective view in FIG. 4, clamp 51 is clamped onto umbilical cord 49 by pressing the arms together, until tapered ends 24 (FIG. 1) and 25 of arms 12 and 16, respectively, are ratcheted as deeply as possible into locking teeth 20 (FIG. 1) and 21, respectively. Splash guards 33 (FIG. 3) and 42 help maintain the position of umbilical cord 49 when the clamp is closed.

Clamps 10 and 11 can be opened and removed in an emergency by pulling front splash guards 15 and 19 outwardly to release tapered ends 24 (FIG. 1) and 25 from locking teeth 20 (FIG. 1) and 21, respectively.

DESCRIPTION FIG. 5

Figure 5:
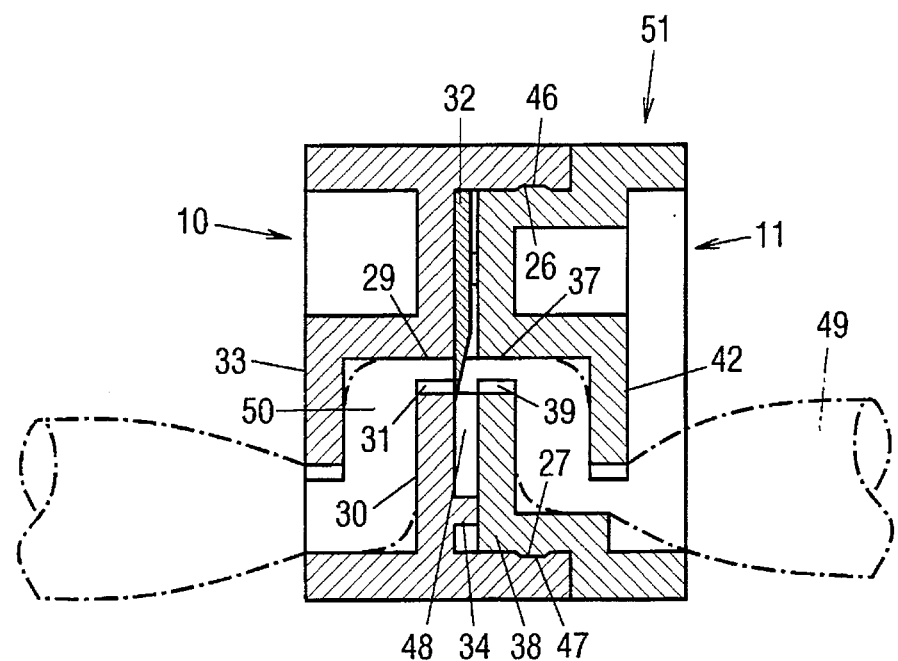
FIG. 5 is a sectional view of the umbilical cord cutting and clamping device, taken along line 5—5 in FIG. 4.
Figure 6:
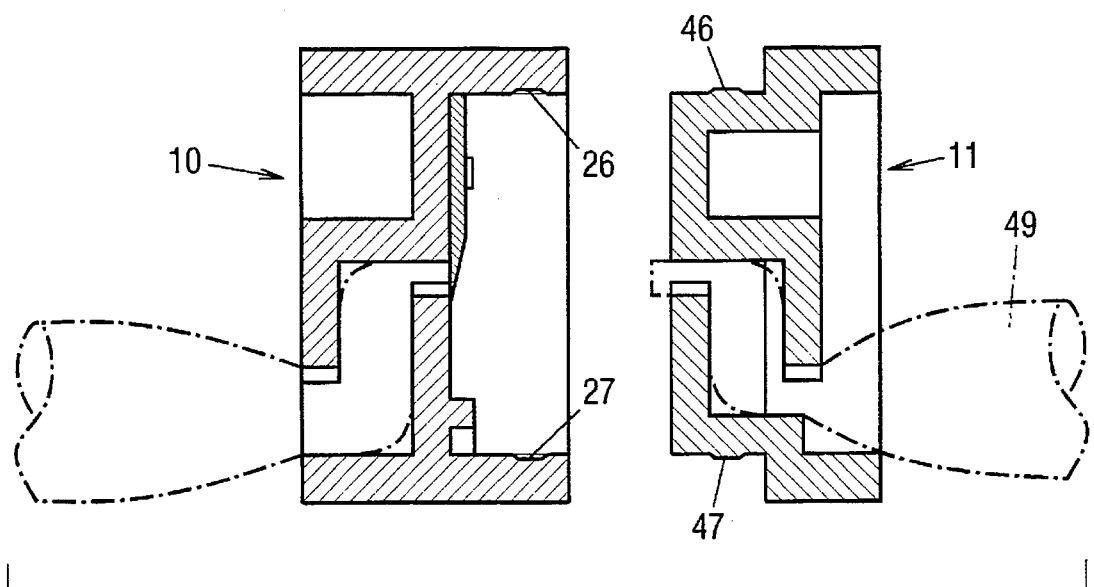
FIG. 6 is a sectional view of the umbilical cord cutting and clamping device in a separated condition.

The umbilical cord cutting and clamping device is shown in FIG. 5 in a sectional view taken along line 5—5 in FIG. 4. Clamps 10 and 11 are securely held together as clamp 51 by the interlocking of ribs 46 and 47 in grooves 26 and 27, respectively, so that they resist accidental separation or unlocking.

When clamp 51 is closed, umbilical cord 49 is tightly clamped between gripping surfaces 29 and 31, and between gripping surfaces 37 and 39, and is simultaneously severed by blade 32. Gap 48 provides clearance for the cutting edge of blade 32. Gripping members 30 and 38 are positioned intermediate side splash guards 33 and 42, so that a U-shaped channel 50 is formed. A portion of umbilical cord 49 is formed into a "U" shape by channel 50.

During the closing of clamp 51, when umbilical cord 49 is initially penetrated by blade 32, any blood ejected therefrom is prevented by side splash guards 33 and 42 from splashing out the sides of clamp 51, and by from splash guards 15 (FIG. 4) and 19 (FIG. 4) from splashing out the front thereof. When clamp 51 is fully closed, it is tightly clamped on umbilical cord 49 to eliminate further blood loss from either severed end thereof. The umbilical cord cutting and clamping device thus conveniently severs and clamps an umbilical cord in a single stroke.

DESCRIPTION FIG. 6

After the clamp is installed, the baby is separated from the placenta by pulling clamps 10 and 11 away from each other with moderate force, so that ribs 46 and 47 are snapped out of grooves 26 and 27, respectively. Clamp 10 remains tightly clamped on the placenta's side of the umbilical cord, and clamp 11 remains tightly clamped on the baby's side of the umbilical cord.

The placenta is removed from the mother, and discarded with clamp 10. Clamp 11 remains on the baby's umbilical cord, which will dry and naturally separate from the baby in about two weeks. Alternatively, another umbilical cord clamp (not shown) can be clamped onto the baby's remaining umbilical cord, and clamp 11 can be removed and discarded.

CONCLUSION, RAMIFICATIONS, AND SCOPE

Accordingly the reader will see that we have provided an umbilical cord cutting and clamping device that severs and clamps an umbilical cord in a single stroke. It is very easy to install. It prevents blood from splashing onto surrounding persons during the cutting process, and it eliminates further blood loss from the severed ends of the umbilical cord immediately after it is cut. It includes two clamps that resist accidental separation or unlocking. The clamps are easily separable, when desired, after installation to allow the newborn baby to be detached from the placenta. It includes only three components, so that it is very economical to manufacture.

Although the above descriptions are specific, they should not be considered as limitations on the scope of the invention, but only as examples of the preferred embodiment. Many other ramifications and variations are possible within the teachings of the invention. For example, the clamps can be made of other suitable materials. Knurls can be provided on the outside of the second arms. Therefore, the scope of the invention should not be determined by the examples given, but by the appended claims and their legal equivalents.

We claim:

1. An umbilical cord clamp, comprising:

first and second arms hingeably connected at a first end for clamping around an umbilical cord, each arm including a gripping surface for gripping said umbilical cord when said arms are clamped thereon;

a blade fixedly attached to said first arm for simultaneously severing said umbilical cord when said arms are clamped thereon, said blade having opposite sides and a forward cutting edge projecting toward said second arm, said cutting edge cooperating with said second arm to cut said umbilical cord when said arms are clamped thereon into a space between said arms; and a pair of side splash guards positioned on either side of said blade and projecting substantially ahead of said cutting edge, said side splash guards for preventing blood from splashing out of said umbilical cord clamp when said umbilical cord is severed.

2. The umbilical cord clamp of claim 1, further including locking means for locking said arms in a clamped position when said arms are clamped around said umbilical cord.

3. The umbilical cord clamp of claim 2 wherein said locking means is unlockable for opening and unclamping said arms.

4. The umbilical cord clamp of claim 1, further including a front splash guard attached to a second end of one of said arms and extending toward a second end of another one of said arms for preventing blood from splashing out a front side of said umbilical cord clamp.

5. An umbilical cord cutting and clamping device, comprising:

a pair of clamps each including a pair of arms hingeably connected at a first end for clamping around an umbilical cord, each arm including a gripping surface for gripping said umbilical cord when said clamps are clamped thereon;

detachable retaining means for detachably retaining said clamps in a side-by-side abutting relation;

a blade fixedly attached to one of said arms of one of said clamps for simultaneously severing said umbilical cord when said clamps are clamped thereon, said blade having opposite sides and a forward cutting edge projecting toward another one of said arms of said one of said clamps, said cutting edge cooperating with said another one of said arms to cut said umbilical cord when said clamps are clamped thereon and a pair of side splash guards positioned on either side of said blade and projecting substantially ahead of said cutting edge, said side splash guards for preventing blood from splashing out of said umbilical cord cutting and clamping device when said umbilical cord is severed; whereby said clamps are separable after clamping onto and severing said umbilical cord.

6. The umbilical cord cutting and clamping device of claim 5, further including locking means for locking said clamps in a clamped position when said clamps are clamped around said umbilical cord.

7. The umbilical cord cutting and clamping device of claim 6 wherein said locking means is unlockable for opening and unclamping said clamps.

8. The umbilical cord cutting and clamping device of claim 5, further including a from splash guard attached to a second end of one of said arms and extending toward a second end of another one of said arms for preventing blood from splashing out a front side of said umbilical cord cutting and clamping device.

9. The umbilical cord cutting and clamping device of claim 5 wherein each clamp generally forms a "U" shape, each arm including an interior surface on an interior of said "U", said detachable retaining means comprises a retaining groove positioned on said interior surface of each arm of one of said clamps, a pair of members extending from another one of said clamps and engaging said interior surfaces of said one of said clamps, and a retaining rib arranged on each member in latching engagement with a corresponding retaining groove, so that said clamps are securely held together, and can be pulled apart by snapping said ribs out of said grooves.

10. An umbilical cord cutting and clamping device, comprising:

first and second clamps each including first and second arms hingeably connected at a first end for clamping around an umbilical cord, each arm including a gripping surface for gripping said umbilical cord when said clamps are clamped thereon;

detachable retaining means for detachably retaining said clamps in a side-by-side abutting relation;

a blade rigidly attached to said first arm of said first clamp, said blade having opposite a forward cutting edge projecting toward said second arm of said first clamp, said cutting edge cooperating with said second arm of said first clamp for simultaneously severing said umbilical cord when said clamps are clamped thereon; and a side splash guard attached to said first arm of said first clamp and another side splash guard attached to said first arm of said second clamp, so that said side splash guards are positioned on either side of said blade, said side splash guards extending substantially ahead of said cutting edge of said blade, so that when said arms are clamped around said umbilical cord, said gripping surfaces of said second arms are positioned between said side splash guards so as to form a U-shaped channel for said umbilical cord, said side splash guards preventing blood from splashing out of said umbilical cord cutting and clamping device when said umbilical cord is severed;

whereby said clamps are separable after clamping onto and severing said umbilical cord.

11. The umbilical cord cutting and clamping device of claim 10, further including locking means for locking said clamps in a clamped position after said clamps are clamped around said umbilical cord.

12. The umbilical cord cutting and clamping device of claim 11 wherein said locking means is unlockable for opening and unclamping said clamps.

13. The umbilical cord cutting and clamp device of claim 10, further including a front splash guard attached to a second end of one of said arms of one of said clamps and extending toward a second end of another one of said arms of said one of said clamps for preventing blood from splashing out a front side of said umbilical cord clamp.

14. The umbilical cord cutting and clamping device of claim 10 wherein each clamp generally forms a "U" shape, each arm including an interior surface on an interior of said "U", said detachable retaining means comprises a retaining groove positioned on said interior surface of each arm of one of said clamps, a pair of members extending from another one of said clamps and engaging said interior surfaces of said one of said clamps, and a retaining rib arranged on each member in latching engagement with a corresponding retaining groove, so that said clamps are securely held together, and can be pulled apart by snapping said ribs out of said grooves.

* * * * *